United States Patent [19]

Lindstrom et al.

[11] Patent Number: 5,204,325
[45] Date of Patent: * Apr. 20, 1993

[54] VISCOELASTIC SOLUTION

[76] Inventors: Richard L. Lindstrom, 1741 Archer Ct., Plymouth, Minn. 55447; Debra Skelnik, P.O. Box 758 Rte. 1, Cambridge, Minn. 55008

[*] Notice: The portion of the term of this patent subsequent to Dec. 15, 2004 has been disclaimed.

[21] Appl. No.: 695,332

[22] Filed: May 3, 1991

Related U.S. Application Data

[62] Division of Ser. No. 284,533, Dec. 15, 1988.

[51] Int. Cl.$^5$ ............... A61K 37/00; A61K 37/26; A61K 37/36
[52] U.S. Cl. ..................... 514/4; 514/3; 514/12; 514/21
[58] Field of Search ............ 514/4, 3, 21, 12

[56] References Cited

U.S. PATENT DOCUMENTS 4,713,375 12/1987 Lindstrom et al. ............ 514/57
5,013,714 5/1991 Lindstrom et al. ............ 514/4

OTHER PUBLICATIONS

Skelnik et al., Invest. Ophthalmol. Visual Sci 28 (3 Suppl) 1987, p. 326.
Couch et al., "Mitotic Activity of Corneal Endothelial Cells in Organ Culture with Recombinant Human Epidermal Growth Factor", Ophtalmology, Jan., 1987, vol. 94, No. 1, pp. 1-4.

Primary Examiner—Merrell C. Cashion, Jr.
Assistant Examiner—Choon Koh
Attorney, Agent, or Firm—Hugh D. Jaeger

[57] ABSTRACT

Viscoelastic solution including a buffered solution, 0.01-8% chondroitin sulfate, 0.1-8% hydroxypropyl methylcellulose, pH adjusted to 6.0-8.0 at a osmolality between 200-400 mOsmol/L. The buffered solution can be HEPES buffered minimum essential media (MEM), phosphate buffer saline (PBS), buffered balanced salt solution, or TC199. A cell growth factor or cell growth supplement is included in the solution.

6 Claims, No Drawings

VISCOELASTIC SOLUTION

This application is a divisional of U.S. Ser. No. 07/284,533, filed Dec. 15, 1988, entitled "Viscoelastic Solution".

BACKGROUND OF THE INVENTION

1. Field of the Invention

The present invention pertains to a viscoelastic solution which is used during eye surgery to protect cells from mechanical trauma, to maintain or create tissue spaces, to ensure separation and lubrication of tissue surfaces, to permit the manipulation of tissues without mechanical damage, and to provide cell growth factors, cell supplements and/or basement membrane components that support ocular wound healing.

2. Description of the Prior Art

There have been numerous prior art solutions such as Healon, a non-inflammatory, high molecular weight fraction of sodium hyaluronate.

One such viscoelastic solution is described in U.S. Pat. No. 4,713,375 to Lindstrom and Skelnik, issued on Dec. 15, 1987.

The present invention provides a viscoelastic solution which includes good coating properties and a naturally occurring biocompatible polymer.

SUMMARY OF THE INVENTION

The general purpose of the present invention is a viscoelastic solution which provides a buffered pH neutral solution as a base, and includes the attributes of the combination of chondroitin sulfate and hydroxypropyl methylcellulose. A cell growth factor, cell growth supplement or basement membrane component is also added to the solution.

One significant aspect and feature of the present invention is a viscoelastic solution which provides better viscosity including the viscous properties of the hydroxypropyl methylcellulose and the lubricating properties of chondroitin sulfate.

Another significant aspect and feature of the preset invention is providing a buffered pH neutral solution as a base for the viscoelastic solution.

A further significant aspect and feature of the present invention is a viscoelastic solution which provides cell protection and cell coating during eye surgery. The solution provides maintenance of the tissue space, the chondroitin sulfate lubricates the tissue while the hydroxypropyl methylcellulose provides tissue manipulation.

A still further significant aspect and feature of the present invention is a viscoelastic solution with a cell growth factor, cell growth supplement, or basement membrane component that supports corneal wound healing.

DESCRIPTION OF THE PREFERRED EMBODIMENTS

Viscoelastic solution includes a buffered solution, 0.1-8% hydroxypropyl methylcellulose and 0.01-8% chondroitin sulfate, pH adjusted to 6.0-8.0, and having an osmolality of 200-400 mOsm/L. The buffered solution can be selected from HEPES buffered minimum essential media (MEM), phosphate buffer saline (PBS), buffered salt solution, or tissue culture medium 199. The hydroxypropyl methylcellulose can be substituted with either carboxypropyl methylcellulose or a cellulose gum, dextran or dextran sulfate. Preferably, the hydroxypropyl methylcellulose is present at a concentration of 0.01-10% while the chondroitin sulfate can be present at a concentration of 0.01-10 percent by volume. The solution ca be introduced into the eye during surgery to protect cells from trauma, to provide lubrication during the procedure, and to promote ocular wound healing.

Cell growth factors or growth supplements which can be used are:

1. Fibroblastic growth factor (FGF), a single chain polypeptide, isolated and purified from the pituitary, human (hFGF) fibronectin or bovine fibronectin (bFGF), in either the acidic or basic forms. The molecular weight range is 14,000 to 16,000. This factor has been demonstrated mitogenic in vitro to a wide variety of cells comprising mesoderm and neuroectoderm tissue.

This also includes synthetic formulated FGF basic peptides consisting of: (1-24)

Pro-Ala-Leu-Pro-Glu-Asp-Gly-Gly-Ser-Gly-Ala-
Phe-Pro-Pro-Gly-His-Phe-Lys-Asp-Pro-Lys-Arg-
Leu-Try and synthetic formulated FGF acidic peptides consisting of: (1-11)

Phen-Asn-Leu-Pro-Leu-Gly-Asn-Tyr-Lys-Lys-Pro

The fibroblastic growth factor can be used at concentrations of 0.1 ng/ml-100 mg/ml.

2. Endothelial Cell Growth Factor (ECGF), prepared from the hypothalamus as a lyophilized extract. This growth supplement has been demonstrated mitogenic in vitro to a wide variety of endothelial cells; i.e., human corneal endothelial cells, human umbilical vein endothelial cells, and mouse Balb/c fibroblasts.

The Endothelial Cell Growth Factor can be used at concentrations of 200 ug/ml-500 mg/ml.

3. Urogastrone or Epidermal Growth Factor (EGF), a single chained polypeptide, is composed of 53 amino acids, containing 3 disulfide bonds and has been isolated from mouse submaxillary glands (mEGF) and human urine (hEGF). This growth factor has been demonstrated to be mitogenic in vitro for a wide variety of cells of ectodermal and mesodermal origin.

This also includes synthetic mouse EGF:

Asn-Ser-Tyr-Pro-Gly-Cys-Pro-Ser-Ser-Tyr-Asp-
Gly-Tyr-Cys-Leu-Asn-Gly-Gly-Val-Cys-Met-
His-Ile-Glu-Ser-Leu-Asp-Ser-Tyr-Thr-Cys-Asn-
Cys-Val-Asp-Arg-Cys-Gln-Thr-Arg-Asp-Leu-
Arg-Trp-Trp-Glu-Leu-Arg

And synthetic EGF [Cys(Acm) 20'31] (20-31)

Cys-(Acm)-Met-His-Ile-Glu-Ser-Leu-Asp-Ser-Tyr-
Thr-Cys(Acm)

The Epidermal Growth Factor can be used at concentrations of 0.1 ng/ml-100 mg/ml 4. Bovine pituitary extract (BPE), an aqueous extract of bovine or human pituitary glands. This growth supplement has been demonstrated mitogenic in vitro to a wide variety of epithelial cells; i.e., human corneal epithelium, human epidermal keratinocytes The Bovine Pituitary Extract can be used at concentrations of: 0.1 ng/ml-500 mg/ml 5. Insulin, a polypeptide hormone that functions in the regulation of cellular carbohydrate metabolism and the synthesis of cellular protein, RNA and neutral lipids.

Insulin can be used at concentrations of 0.1 ug/ml–10 mg/ml

6. Transferrin used at 0.1 ug/ml–10 mg/ml
7. Sodium Selenite used at 0.1 ng/ml–100 ug/ml
8. Platelet-derived growth factor (PDGF) a polypeptide stored in platelets and released into serum during clotting, has been shown to be a mitogen for cultured fibroblast cells.

Platelet-derived growth factor can be used at 0.1 ng–500 mg/ml

9. An aqueous extract of bovine or human retinas. This growth supplement has demonstrated mitogenic in vitro to a wide variety of endothelial cells, i.e., human corneal endothelium and human vascular endothelium.

Retinal derived growth factor can be used at 0.1 ng/ml–10 mg/ml

10. Insulin-like growth factor: IGF-1; a single-chain polypeptide with a molecular weight of 7,650 daltons (76 amino acids) and a pI of 8.2 to 8.4. IGF-1, also known as Somatomedin C, is the anabolic basis polypeptide that functions as the mitotic messenger for pituitary growth hormone.

Insulin-like growth factor can be used at 0.1 ng/ml–10 mg/ml

11. Transforming Growth Factor—Beta TGFB: TGFB has a molecular weight of 25,000 daltons and is a homodimer composed of two identical 112-amino acid chains.

TGFB can be used at 0.1 ng/ml–10 mg/ml

12. Transforming Growth Factor—Alpha: TGF-alpha can be used at 0.1 ng/ml–10 mg/ml 13. Glycosaminoglycans: All used at a concentration of 0.01–10%:
  1. dermatin sulfate
  2. heparin sulfate
  3. heparan sulfate
  4. keratin sulfate
  5. hyaluronic acid 14. Antioxidants:
  1. ascorbic acid, concentration of 0.001–10 mM
  2. glutathione, concentration of 0.001–10 mM
  3. DL- -tocopherol, concentration of 0.001–10 mM
  4. 2-meroaptoethanol 0.001–10 mM 15. Glycoproteins that promote cellular adhesion and migration (wound healing):
  1. Laminin, a large glycoprotein having a molecular weight of approximately 1,000,000 daltons. The laminin molecule has the shape of an asymmetric cross, comprised of 3B chains of 200,000 daltons each, and one A chain of 400,000 daltons. The chains are held together by disulfide bonds. The single A chain contains a binding site for heparin sulfate. The B chains contain type IV collagen binding sites. The intersection of the three B chains is the locus for cell binding. Laminin provides cells with physiological compatible extracellular matrix that will foster attachment, cytoplasmic spreading and proliferation.

Laminin can be used at 0.01 ug/ml–10 mg/ml.

2. Fibronectin is an extracellular matrix-associated glycoprotein composed of two disulfide bonded subunits of 220,000 daltons each. Fibronectin has the potential to interact with several cell surface associated macromolecules including collagen, glycosaminoglycans and cell surface receptors. Fibronectin promotes cell adhesion and migration of human corneal endothelial cells, epithelial cells and fibroblasts.

Fibronectin can be used at 1 ng/ml–10 mg/ml

16. Extracellular Matrix Components:
  A. A collagen used in the range 1 ng/ml–1 g/ml selected from the group:
    1. Type I collagen;
    2. Type II collagen;
    3. Type III collagen;
    4. Type IV collagen;
    5. Type V collagen; or,
  B. Enactin, used at 1 ng/ml–10 mg/ml
  C. Insulin-like growth factors: IGF1 used at 0.1 ng/ml–10 mg/ml
  D. Transforming growth factors: TGF alpha and TGF Beta used at 0.1 ng/ml–10 mg/ml Various modifications can be made to the present invention without departing from the apparent scope hereof.

We claim:

1. A viscoelastic composition comprising:
   a. a buffered balanced salt solution;
   b. hydroxypropyl methyl cellulose; and,
   c. a glycosaminoglycan which is dermatin sulfate, heparin sulfate, heparan sulfate, keratin sulfate or hyaluronic acid;
the composition having a pH of 6.0–8.0 and an osmolality of 200–400 mOsmol/L.

2. A viscoelastic composition comprising:
   a. a buffered balanced slat solution;
   b. hydroxypropyl methyl cellulose;
   c. a glycosaminoglycan; and,
   d. at least one growth factor or growth supplement;
the composition having a pH of 6.0–8.0 and an osmolality of 200–400 mOsmol/L.

3. The composition of claim 2 wherein the glycosaminoglycan is dermatin sulfate, heparin sulfate, heparan sulfate, keratin sulfate or hyaluronic acid.

4. A viscoelastic composition comprising:
   a. a buffered balanced salt solution;
   b. hydroxypropyl methyl cellulose;
   c. Epidermal Growth Factor (EGF); and,
   d. a glycosaminoglycan which is dermatin sulfate, heparin sulfate, heparan sulfate, keratin sulfate or hyaluronic acid;
the composition having a pH of 6.0–8.0 and an osmolality of 200–400 mOsmol/L.

5. A viscoelastic composition comprising:
   a. a buffered balanced slat solution;
   b. hydroxyropyl methyl cellulose;
   c. a glycosaminoglycan;
   d. Epidermal Growth Factor (EGF); and,
   e. insulin;
the composition having a pH of 6.0–8.0 and an osmolality of 200–400 mOsmol/L.

6. The composition of claim 5 in which the glycosaminoglycan is dermatin sulfate, heparin sulfate, heparan sulfate, keratin sulfate or hyaluronic acid.

* * * * *